United States Patent [19]

Klimek

[11] 4,270,255

[45] Jun. 2, 1981

[54] METHOD OF MANUFACTURING A SWASH PLATE ASSEMBLY

[75] Inventor: Edmund J. Klimek, Arlington Heights, Ill.

[73] Assignee: Borg-Warner Corporation, Chicago, Ill.

[21] Appl. No.: 24,219

[22] Filed: Mar. 26, 1979

[51] Int. Cl.³ .............................................. B23P 15/00
[52] U.S. Cl. ......................... 29/156.5 A; 29/156.4 R; 29/469
[58] Field of Search .................... 29/156.5 A, 156.5 R, 29/156.4 R, 469; 74/579 R, 579 E; 91/499

[56] References Cited

U.S. PATENT DOCUMENTS

| 907,096 | 12/1908 | Strom | 74/579 E |
|---|---|---|---|
| 1,392,389 | 10/1921 | Anderson | 74/579 |
| 1,548,382 | 8/1925 | Paul | 403/25 |
| 1,851,670 | 3/1932 | Hait, Jr. | 74/579 |
| 2,107,795 | 2/1938 | Larsh | 309/20 |
| 2,252,351 | 8/1941 | Paulus | 29/149.5 |
| 2,361,046 | 10/1944 | Molly | 29/156.5 A |
| 3,763,535 | 10/1973 | Gallagher | 29/156.5 R |
| 3,903,753 | 9/1975 | Ottl et al. | 74/579 E |

FOREIGN PATENT DOCUMENTS 1360981  4/1964  France ........................................ 91/499

Primary Examiner—Daniel C. Crane
Attorney, Agent, or Firm—Thomas B. Hunter

[57] ABSTRACT

An improved method of manufacturing a swash plate assembly for use in a compressor, fluid motor or similar device in which a plurality of pistons are connected, by means of connecting rods, to a swash plate which drives (or is driven by) the pistons. A plurality of piston assemblies are made by casting the piston body around one end of a connecting rod section which is formed with a ball, thus providing a ball-socket connection therebetween. Other connecting rod sections are cast-in-place and captured in sockets within the wobble plate. With the connecting rod being made in two pieces, the section connected to each of the pistons and the section connected to the swash plate are positioned in a fixed relation to one another in an appropriate fixture. The two sections of each connecting rod are then secured to each other, such as by welding, brazing or crimping, to complete the assembly.

3 Claims, 4 Drawing Figures

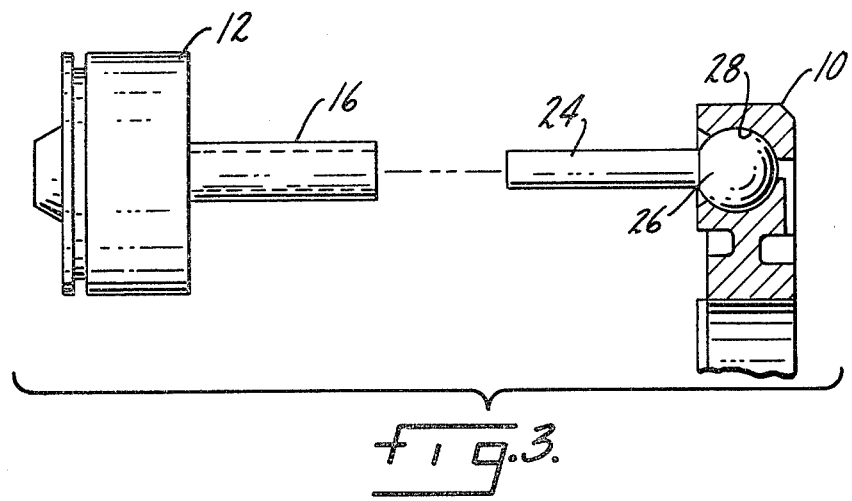
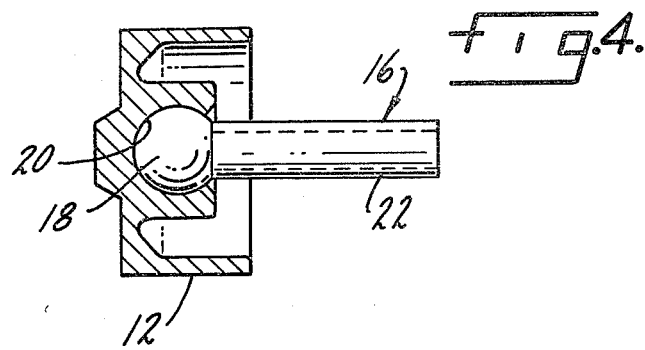

METHOD OF MANUFACTURING A SWASH PLATE ASSEMBLY

BACKGROUND OF THE INVENTION

1. Field of the Invention

A method of manufacturing a compressor or fluid motor generally classified in Class 29, Subclass 156.4R.

2. Description of the Prior Art

U.S. Pat. No. 1,548,382 (J. A. Paul) discloses a piston and connecting rod construction in which the connecting rod is formed in two pieces with a threaded connection therebetween so as to permit adjustment between the crown of the piston and the center line of the bearing engaging the crankshaft. This patent fails to disclose the cast-in-place technique for either the piston to connecting rod joint or the connecting rod to swash plate joint (and it does not disclose a swash plate per se).

U.S. Pat. No. 2,107,795 (E. P. Larsh) also discloses a two piece connecting rod in which the portion of the rod which is connected to the piston comprises a tube which fits telescopically over a shank portion of the connecting rod bearing section. This disclosure is deficient for essentially the same reasons as the Paul patent.

U.S. Pat. No. 2,252,351 (W. Paulus) is one of the earliest disclosures of a cast-in-place technique for forming a ball and socket connection between two parts.

U.S. Pat. No. 3,763,535 (Gallagher) is directed to a method of forming a ball and socket connection between a connecting rod and a piston. The alleged novelty concerns the use of a selected pressure for the molten material introduced into the mold cavity during the die casting process.

SUMMARY OF THE INVENTION

This invention relates to a new and improved method of manufacturing a swash plate and piston assembly of the type including a plurality of pistons connected to a swash plate such that axial motion is transmitted to said pistons by the nutating motion of said swash plate. If the assembly is to be used in a fluid motor, the reciprocating motion of the pistons would drive the swash plate.

The basic manufacturing steps include: (1) fabricating a plurality of piston subassemblies, each of which is made by providing a first connecting rod section with one end thereof formed with a substantially spherical surface, and then die casting a piston so that the spherical surface is cast in a complementary socket to form a ball/socket connection; (2) providing a plurality of second connecting rod sections each having one end formed with a spherical surface; (3) die casting a swash plate such that the ends of each second connecting rod section are captured in a complementary socket to form ball/socket connections between said swash plate and said second connecting rod sections; (4) supporting said pistons at a fixed position relative to said swash plate; and (5) joining said first and second connecting rod sections together. Appropriate finishing procedures can be carried out on the piston subassemblies after they are made and on the swash plate subassembly after it has been cast with the connecting rod sections associated therewith.

DESCRIPTION OF THE DRAWINGS

FIG. 3 is an exploded assembly drawing illustrating the relationship of the piston subassembly and the swash plate subassembly prior to being secured to one another; and FIG. 4 is a detailed cross section view of a piston subassembly.

DETAILED DESCRIPTION OF THE INVENTION

Figure 1:
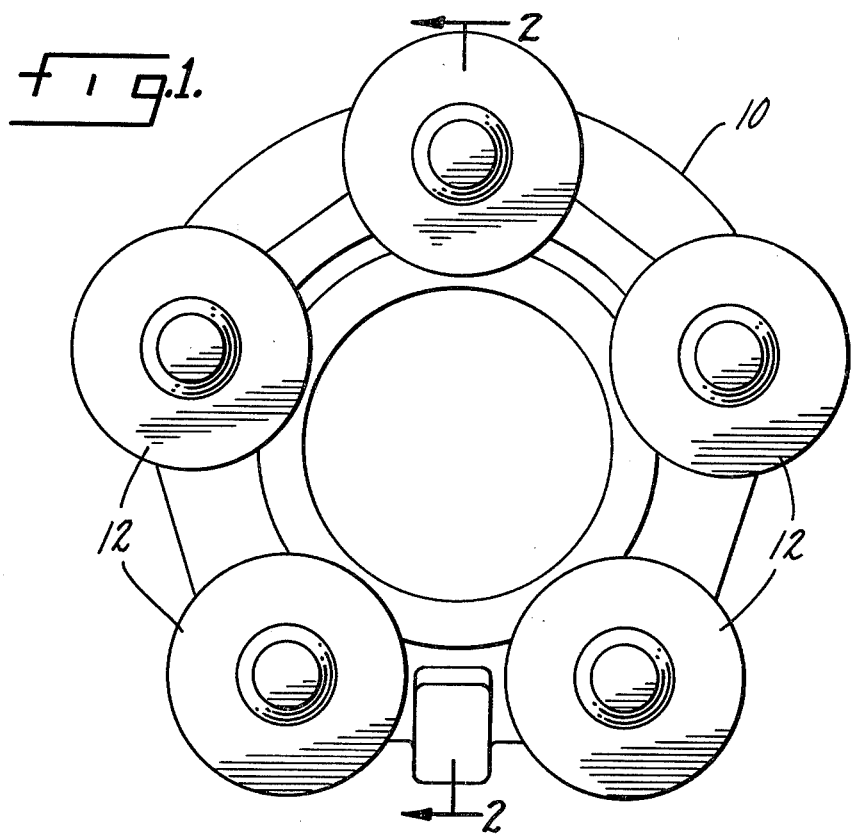
FIG. 1 is a plan view of a swash plate assembly constructed in accordance with the principles of the present invention.

The present invention provides a method of conveniently and accurately connecting ball and socket assemblies by joining of telescoping sections of connecting rods. Ball and socket assemblies are used extensively to allow combinations of axial, rotational and orbital movements in machinery. Such machinery components include pistons, drive plates and crank shafts in pumps and compressors, actuating toggles for presses and punches, connecting rods and assemblies in conveyor systems. They are very suitable for use in swash plate assemblies and that is what is described in the present specification.

Depending on the accuracy and/or strength required of the ball and socket joint, there are several methods for constructing the assembly. As examples: a round aperture with a spherical bottom is machined into the socket member. This requires accurate and expensive tooling. After the ball with its stem or other attachment is placed into the aperture, the wall of the aperture must be made to enclose the ball to retain it in the socket during its motion. The enclosing can be accomplished by rolling, swaging, pressing, spinning or any metal deforming process where the aperture wall is deformed to conform around the ball to the degree required for strength of the joint and to allow the required freedom of movement. Any of these current methods is a separate operation in manufacture of the assembly and the method is selected dependent on economy, degree of accuracy or tightness required of the joint and also to a degree on the materials of construction of both ball and socket.

To produce strong assemblies, capable of withstanding repeated heavy loads or to produce precise assemblies with a controlled or minimum movement or "play" between the ball and socket, a maximum amount of conformity of the ball to socket must be achieved. This high degree of conformity requires large deformations of the socket material which requires more time consuming and expensive procedures and equipment. The maximum "fit" also demands a large degree of deformation of the socket material which may require the use of soft, weak material by necessity and which may still result in cracking or stresses that act to further weaken the assembly.

The high pressures required to deform the walls of the aperture to conform to the ball require that the ball be made of a high strength material that will resist crushing during forming. This limits the selection of ball materials with possible penalties in desired properties or economy.

Aside from the problems cited above, the high pressures of forming do not assure full conformity to the spherical surface of the ball. As a result of incomplete forming, and also because of wrinkling and buckling of the deformed materials, the applied loads are not uniformly distributed over the spherical surface of the ball. This results in concentrated loads which cause overloading and failure. Load concentrations also cause excessive wear on the contact points which increases the amount of relative movement in the socket which complicates loading and leads to premature failure.

Any and all of the methods of assembling the ball to the socket are such that precise dimensions of the assembly cannot be maintained. In many applications, two or more ball socket joints are connected to form the piece of machinery. Final dimensioning of the apparatus must be performed by machining of the unwieldly assembly.

In many of the mechanical forming processes, a spacer material or coating on either the ball or both components is employed to assure that some or a specified amount of relative movement will exist between ball and socket if only to assure free movement. These "spacers" must be removed by dissolving, heating or mechanical means.

Other methods of forming the ball socket assembly include the use of wires, rods or pins which prevent the escape of the ball from the socket. These require secondary operations to fix the retainer to the socket body. Another method would be to machine spherical apertures into two separate sections then connect the separate sections after enclosing the ball. The connecting could be by fasteners, springs, brazing, etc.

A preferred method for manufacture of ball and socket junctions includes the technique of inserting the ball and its appendages during manufacture of the socket by molding of liquid, superplastic or powdered metals or polymeric compounds, and preferably by die casting of molten metal, such as aluminum.

The pistons of a variable displacement pump, compressor or fluid motor are attached to a driving plate by connecting rods. The movements of both the pistons and drive plate require the flexibility of a ball-socket junction. The assembly can contain a multiple number of pistons attached to the swash plate. The pistons must be machined for dimensions, contour and ring grooves on the OD and top surfaces. On the other hand, the swash plate must be machined on the bottom and ID surfaces for contour and flatness. The final assembly of pistons and swash plate must be dimensioned to a tolerance of 0.001"–0.002" in final length.

Figure 2:
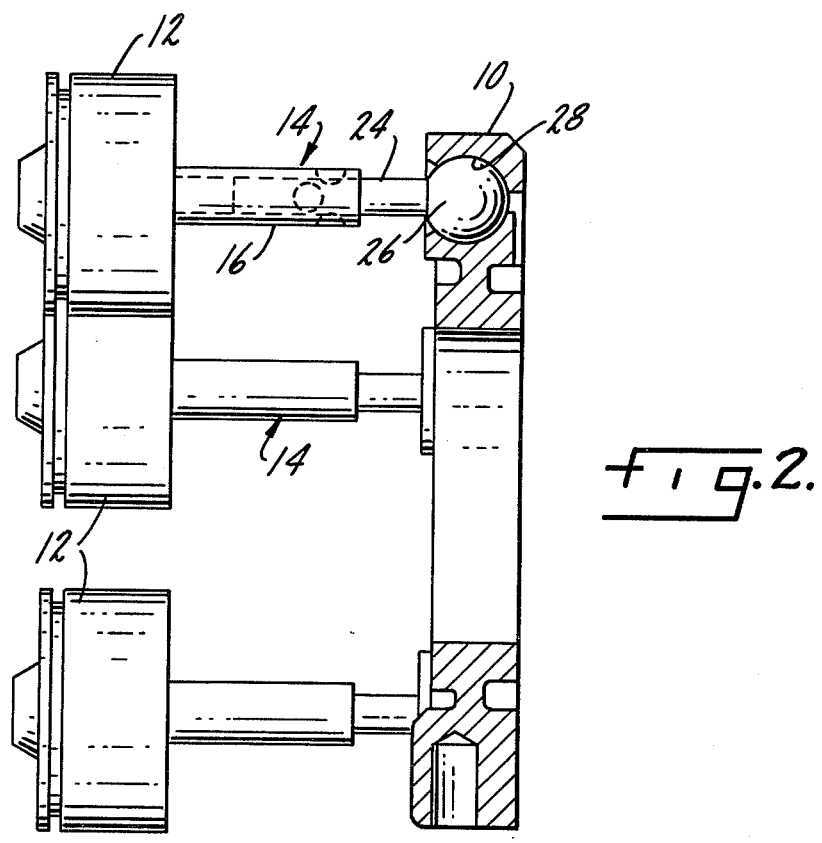
FIG. 2 is a cross section view taken along the plane of line 2—2 of FIG. 1.

Referring to the drawings, and particularly to FIGS. 1 and 2, the swash plate assembly is formed of a swash plate 10 and a plurality of pistons 12 with connecting rods 14 extending between the pistons and swash plate. Each connecting rod is made up of a first section 16 having a spherical end 18 (FIG. 4) which is captured in a socket 20 formed in the base of the piston. Extending from the connecting rod end 18 is a straight tubular portion 22 which telescopes over a second connecting rod section 24. The latter has a spherical end 26 which is captured in a complementary socket 28 to form a ball and socket connection between connecting rod section 24 and the swash plate 10.

The foregoing generally describes the completed swash plate assembly. In the manufacture of the assembly, the following preferred procedure is used:

1. The steel ball 18 is joined to a section of hollow tubing 22. The tubing is about ¼" longer than one-half the final length of the connecting rod. The ball and stem assembly so formed in coated with a mold release agent and heated to 300° to 400° F. to drive off any volatiles in the coating, to preheat the ball and to stress relieve the weld.

2. The coated, preheated ball and stem are placed into the cavity of a die casting machine as described in U.S. Pat. No. 3,763,535. The mold is closed and a casting made as per conventional die casting procedures.

3. After ejection of the solidified casting containing the ball and stem insert, the piston is machined to final dimensions.

4. The swash plate 10 is produced by inserting the required number of welded, coated and preheated ball-stem assemblies 24, 26 into the mold cavity and the casting poured and ejected. The swash plate casting with inserts is machined to final dimensions.

5. The piston and swash plate subassemblies are placed into a fixture (not shown) which holds all of the components in proper position for joining of the connecting rods at their center area and also fixes the total length of the assembly to within required dimensions prior to joining.

6. The male-female junction at the center of the connecting rod is joined together by resistance welding to complete the assembly.

As examples of specific variations of materials and processes inferred to above and to illustrate the scope of the method without limiting the method to the examples, the manufacture of the assembly could be performed by several variations. For example, the materials of construction and method of manufacture of the balls can be of any type as currently available or practiced or of any special type as needed for a particular application. These special properties could include strength, wear or corrosion resistance or magnetic properties. As example, hard or soft steel, cast irons, copper or aluminum base alloys or nonmetallic balls could be used as desired for properties or economy.

The ball can be attached to the connecting rod section or any appendage by soldering, brazing, resistance or fusion welding, adhesives or by mechanical means such as screw threads. A single piece ball and stem unit could also be included as an insert in the molding process.

The connecting rod section or any appendage can be made of any material by any process to provide the properties and/or economy required of the assembly. As example, the telescoping assembly configuration could be produced by cold heading, swaging, machining, casting or any process known to be used in the shaping of materials. The connecting rods could be made of solid rod or bar, or tubing or combinations of one end solid, the other of tubing. Regardless of method of manufacture, the joining ends at the center of the connecting rods should be such that it can be easily assembled and allow for axial movement to allow final dimensioning.

The coating applied to the ball section prior to molding into the socket could be of a variety of materials and thicknesses as required for properties and economy or to be compatible with the process or materials selected for ball-socket manufacture. As example, hardened steel balls as used for ball bearings, resistance welded to low carbon steel tubing are coated by dipping or spraying with an alcohol dispersion of finely divided graphite. On drying at 400° F. for sufficient time to evaporator all of the alcohol, heat the entire ball-stem and stress relieve the weld, the ball will be coated with a film or graphite. Similar suspensions in water, alcohols or other suspending mediums could be used to deposit films of molybdenum disulfide or other solid lubricants. The coating could be produced by dipping or spraying of polymeric materials of the polyethylene or polybutadiene types which will carbonize without producing large volumes of vapor upon contact with the liquid metal or any source of high temperature to provide a separating film between the ball and socket to assure free motion.

The coating material prevents the sticking of the ball and socket materials by producing an interference film between the two. The thickness of the interference film can be controlled by formulation or by repeated coating to provide a positive or specified clearance as required. Ideally, the coating material would also serve as a lubricant or initial wear-in component in the system as with graphite or carbonized polymer coatings. The selection of the coating material will be dependent on the variables of the assembly including materials, molding process, service conditions, etc. As further example of such selection, a steel ball when inserted into an iron socket casting could be coated with a sodium silicate material that will break up and act as a wear-in abrasive in the joint. Further, a steel ball molded in an aluminum powder compact socket could be coated with a phosphate conversion coating for separation and initial wear-in.

The degree of preheating of the coated ball will be determined by several factors of the coating and the molding process itself. As example, volatile binders and vehicles in the coating must be driven off to prevent large quantities of gas in the mold during molding. The degree of preheat of the insert will also be selected to control the amount of chill and consequent structure, soundness and strength and the amount of shrinkage of the liquid metal cast around the insert.

Several methods are available to those familiar with the art, for securely holding inserts in place during molding of liquid or powdered metals and polymers. These could include adhesives, springs, magnets, vacuum. If required for the design, a core pin in the molding equipment could serve the dual purpose of holding the insert in place and also providing an orifice for lubrication of the socket.

The molding process for forming the socket would be selected based on considerations of materials, special properties, availabilities or economy as required for the type and number of parts being produced. As example, the die casting process mentioned in the example for producing pistons and drive plates was selected on the basis of production quantities (economy) and the type of material required in the piston and plate. The two parts here could be made of aluminum alloy #380. Any other aluminum base alloy compatible with the die casting process and with the required chemical and mechanical properties of the part could be used. Magnesium and zinc based die casting alloys could be used if economy or property requirements allow or demand. Based on the considerations above, any other metal casting process could be used.

The design of the socket is not necessarily limited to containment about the entire periphery of the ball but could be partially slotted to allow greater travel in one or more directions.

Socket manufacture encompassing the present method need not be limited to metals or the casting of liquid metals. The ball inserts as described can be contained in compacted metal powders and processed in the manner known to those familiar with the art for treating metal powder compacts to achieve required properties. The socket could be manufactured by molding or casting of polymeric materials according to procedures well known to those familiar with the arts.

The design or function of the socket is not limited to the piston and drive ring used here as example but could be of any shape required.

The final assembly of the two or more socket assemblies is accomplished by joining the preformed connecting rod sections. As example, for assembly of multiple pistons to a swash plate, the finish machined pistons are fed into a holding fixture which also locates the free moving sections of connecting rods. The drive plate is held in a similar fixture to align its free moving connecting rod sections with the mating ends of the piston rods. The two assemblies are moved together to affect the required final dimension from bottom of the drive plate to top of the pistons. The telescoping ends of the connecting rod sections freely allow such lateral movement. Once the proper dimension is achieved, the holding fixtures are fixed, and the telescoping ends of the connecting rods are joined by a single resistance (spot) weld on each joint. Either multiple welding heads, rotation of holding fixtures or welding head can be utilized to complete all welds as determined by production considerations.

While this invention has been described in connection with certain specific embodiments thereof, it is to be understood that this is by way of illustration and not by way of limitation; and the scope of the appended claims should be construed as broadly as the prior art will permit.

What is claimed is:

1. A method of manufacturing a swash plate assembly comprising the steps of: (1) fabricating a plurality of piston subassemblies, each of which is made by (a) providing a first connecting rod section with one end thereof formed with a substantially spherical surface; and (b) die casting a piston so that a portion of the piston captures said spherical surface in a complementary socket to form a ball/socket connection; (2) providing a plurality of second connecting rod sections each having one end formed with a spherical surface; (3) die casting a swash plate such that the ends of each second connecting rod section are captured in a complementary socket to form ball/socket connections between said swash plate and said second connecting rod sections; (4) supporting said piston subassemblies and said swash plate in a holding fixture to align the respective said first and second connecting rod sections; (5) moving together and telescoping free ends of said connecting rod sections to effect the required final total length dimension from the bottom of said swash plate to the top of said piston subassemblies; and (6) joining said first and second connecting rod sections together of each of said piston subassemblies and said swash plate.

2. A method as defined in claim 1 wherein the piston subassemblies are finish machined prior to being joined to the swash plate.

3. A method as defined in claim 1 wherein said swash plate is finish machined prior to being joined to said piston subassemblies.

* * * * *